US009029581B2

(12) United States Patent
Partin et al.

(10) Patent No.: US 9,029,581 B2
(45) Date of Patent: May 12, 2015

(54) ESTERIFICATION OF FURAN-2,5-DICARBOXYLIC ACID TO A DIALKYL-FURAN-2,5-DICARBOXYLATE VAPOR WITH RECTIFICATION

(71) Applicant: Eastman Chemical Company, Kingsport, TN (US)

(72) Inventors: Lee Reynolds Partin, Kingsport, TN (US); Ashfaq Shaikh, Kingsport, TN (US); Mesfin Ejerssa Janka, Kingsport, TN (US); Kenny Randolph Parker, Afton, TN (US)

(73) Assignee: Eastman Chemical Company, Kingsport, TN (US)

( * ) Notice: Subject to any disclaimer, the term of this patent is extended or adjusted under 35 U.S.C. 154(b) by 0 days.

(21) Appl. No.: 14/491,514

(22) Filed: Sep. 19, 2014

(65) Prior Publication Data

US 2015/0031903 A1 Jan. 29, 2015

Related U.S. Application Data

(62) Division of application No. 13/530,789, filed on Jun. 22, 2012, now Pat. No. 8,859,788.

(51) Int. Cl.
C07D 307/68 (2006.01)
(52) U.S. Cl.
CPC .................................. C07D 307/68 (2013.01)
(58) Field of Classification Search
CPC .................................................... C07D 307/68
USPC .......................................................... 549/485
See application file for complete search history.

(56) References Cited

U.S. PATENT DOCUMENTS

| | | | |
|---|---|---|---|
| 2,551,731 A | 5/1951 | Drewitt | |
| 3,225,066 A | 12/1965 | Lew | |
| 3,845,100 A | 10/1974 | Kusak | |
| 3,852,247 A | 12/1974 | Vizurraga | |
| 4,405,736 A | 9/1983 | Kubota et al. | |
| 4,876,327 A | 10/1989 | Vriesema et al. | |
| 4,977,283 A | 12/1990 | Leupold et al. | |
| 5,958,581 A | 9/1999 | Khanarian et al. | |
| 5,959,066 A | 9/1999 | Charbonneau et al. | |
| 6,025,061 A | 2/2000 | Khanarian et al. | |
| 6,063,464 A | 5/2000 | Charbonneau et al. | |
| 6,063,465 A | 5/2000 | Charbonneau et al. | |
| 6,063,495 A | 5/2000 | Charbonneau et al. | |
| 6,103,825 A | 8/2000 | Frischinger et al. | |
| 6,107,447 A | 8/2000 | Kreuder et al. | |
| 6,126,992 A | 10/2000 | Khanarian et al. | |
| 6,140,422 A | 10/2000 | Khanarian et al. | |
| 6,342,300 B1 | 1/2002 | Bengs et al. | |
| 6,359,070 B1 | 3/2002 | Khanarian et al. | |
| 6,737,481 B1 | 5/2004 | Kurian et al. | |
| 6,914,120 B2 | 7/2005 | Germroth et al. | |
| 7,052,764 B2 | 5/2006 | Chang et al. | |
| 7,385,081 B1 | 6/2008 | Gong | |
| 7,638,592 B2 | 12/2009 | Benecke et al. | |
| 7,700,788 B2 | 4/2010 | Lilga et al. | |
| 8,143,355 B2 | 3/2012 | Matsuda et al. | |
| 8,658,810 B2 | 2/2014 | Shaikh | |
| 8,912,349 B2 | 12/2014 | Shaikh | |
| 2003/0055271 A1 | 3/2003 | Grushin et al. | |
| 2006/0205977 A1 | 9/2006 | Sumner et al. | |
| 2008/0081883 A1 | 4/2008 | King, II et al. | |
| 2008/0182944 A1 | 7/2008 | Benecke et al. | |
| 2009/0018264 A1 | 1/2009 | Fuseya | |
| 2009/0124829 A1 | 5/2009 | Gong | |
| 2009/0143602 A1 | 6/2009 | Benecke et al. | |
| 2009/0156841 A1 | 6/2009 | Sanborn et al. | |
| 2010/0081774 A1 | 4/2010 | Benecke et al. | |
| 2010/0174044 A1 | 7/2010 | Eritate | |
| 2010/0210867 A1 | 8/2010 | Bustamante et al. | |

(Continued)

FOREIGN PATENT DOCUMENTS

| | | |
|---|---|---|
| CA | 2235270 | 4/1997 |
| EP | 0741134 | 11/1996 |

(Continued)

OTHER PUBLICATIONS

Gandini Alessandro, et al., The furan Counterpart of Poly(ethylene terephthalate): An Alternative Material Based on Renewable Resources, Journal of Polymer Science: Part A: Polymer Chemistry, vol. 47, (2009), pp. 295-298.
Partenheimer, Walt et al., Synthesis of 2,5-Diformylfuran adn Furan-2,5-Dicarboxylic Acid by Catalytic Air-Oxidcation of 5-Hydroxymethylfurfural, Unexpectedly Selective Aerobic Oxidation of Benzyl Alcohol to Benzaldehyde with Metal/Bromide Catalysts, Adv. Synth. Catal. 2001, 343, pp. 102-111.
Akutin et al., N.N. USSR Patent 162962, 1964; Chem. Abstr. 1964, 61, p. 8441e.
Lewkowski, J., Synthesis, Chemistry and Applications of 5-Hydroxymethlfurfural and its Derivatiives, ARKIVOC, 2001, pp. 17-54.
Lukes et al., CS Patent 87340 (1959); Chem. Abstr. 1962, 55, p. 17084.
Manasek et al., 1963, 6, 35, Chem. Abstr. 1964, 60, p. 8180a.
Rodivilowa et al., Khim. Tekhnol. 11, 1968, 7, 818, Chem. Abstr. 1969, 70, p. 4685v.
Gonis, George et al., The Preparation of Furan-2,5-dicarboxylic Acid, J. Org. Chem., vol. 27, No. 8, (1962), pp. 2946-2947.

(Continued)

*Primary Examiner* — Taofiq A Solola
(74) *Attorney, Agent, or Firm* — Phan Law Group PLLC (57) ABSTRACT

A process for the manufacture of dialkyl furan-2,5-dicarboxylate (DAFD) vapor composition by feeding furan-2,5-dicarboxylic acid ("FDCA") to an esterification reactor and in the presence of an alcohol compound such as methanol, conducting an esterification reaction to form an esterification vapor containing DAFD, unreacted alcohol compound, 5-(alkoxycarbonyl)furan-2-carboxylic acid (ACFC), and water, and continuously passing the esterification vapor through an ACFC condensing zone, that can be integral with the esterification reactor, in which at least a portion of the ACFC in the esterification vapor is converted to a liquid phase condensate, and continuously discharging the esterification vapor from the ACFC condensing zone as a DAFD vapor. There is also a DAFD vapor composition containing DAFD, water, unreacted alcohol, and by-products.

20 Claims, 4 Drawing Sheets

(56) References Cited

U.S. PATENT DOCUMENTS

| | | |
|---|---|---|
| 2010/0331568 A1 | 12/2010 | Brandvold |
| 2012/0123085 A1 | 5/2012 | Grushin et al. |

FOREIGN PATENT DOCUMENTS

| | | |
|---|---|---|
| FR | 2723946 | 3/1996 |
| JP | 2008291243 | 12/2008 |
| JP | 2008291244 | 12/2008 |
| JP | 2008308578 | 12/2008 |
| JP | 2009215467 | 9/2009 |
| JP | 2009242312 | 10/2009 |
| JP | 2009263509 | 11/2009 |
| WO | 2009118377 | 10/2009 |
| WO | 2009135921 | 11/2009 |
| WO | 2010077133 | 7/2010 |
| WO | 2010132740 | 11/2010 |
| WO | 2010140599 | 12/2010 |
| WO | 2010151346 | 12/2010 |
| WO | 2011023590 | 3/2011 |
| WO | 2011043660 | 4/2011 |
| WO | 2011043661 | 4/2011 |
| WO | 2012101015 | 8/2012 |

OTHER PUBLICATIONS

Lewkowski, J., Convenience Synthesis of Furan-2,5-dicarboxylic Acid and Its Derivatives, Polish J. Chem. 75, (2011), pp. 1943-1946.

Haworth, W.N. et al., The Conversion of Sucrose into Furan Compound, Part II, Some 2: 5-Disubstituted Tetrahydrofurans and their Products of Ring Scission, Journal of the Chemical Society, No. 1, (1945), pp. 1-4.

Search Report and Written Opinion for related PCT Patent Application No. PCT/US2013/044919, dated Aug. 22, 2013, 12 pages.

Search Report and Written Opinion for related PCT Patent Application No. PCT/US2013/044922, dated Sep. 23, 2013, 11 pages.

Sanderson, R.D. et al., Synthesis and Evaluation of Dialkyl Furan-2,5-Dicarboxylates as Plasticizers for PVC, Journal of Applied Polymer Science, vol. 53, No. 13, (1994), pp. 1785-1793.

Yoder, P.A. et al., Ueber Dehydroshleimsaure: eine neue Darstellungsmethode, sowie verschiedene Salze und Ester derselben, Berichte Der Deutschen Chemischen Gesellschaft Abteilung B: Abhandlungen, vol. 34, No. 3, (1901), pp. 3446-3462.

Search Report and Written Opinion for related PCT Patent Application No. PCT/US2013/044927, dated Oct. 18, 2013, 16 pages.

USPTO Restriction Requirement for related U.S. Patent No. 8,658,810, dated May 28, 2013, 8 pages.

USPTO Office Action for related U.S. Patent No. 8,658,810, dated Jul. 26, 2013, 7 pages.

USPTO Notice of Allowance for related U.S. Patent No. 8,658,810, dated Sep. 10, 2013, 6 pages.

USPTO Notice of Allowance for related U.S. Patent No. 8,658,810, dated Jan. 22, 2014, 5 pages.

USPTO Office Action for related U.S. Patent No. 8,912,349, dated Dec. 31, 2013, 12 pages.

USPTO Office Action for related U.S. Patent No. 8,912,349, dated Apr. 11, 2014, 18 pages.

USPTO Notice of Allowance for related U.S. Patent No. 8,912,349, dated Oct. 22, 2014, 5 pages.

ESTERIFICATION OF FURAN-2,5-DICARBOXYLIC ACID TO A DIALKYL-FURAN-2,5-DICARBOXYLATE VAPOR WITH RECTIFICATION

1. CROSS-REFERENCE TO RELATED APPLICATIONS

This application is a divisional of U.S. application Ser. No. 13/530,789, filed Jun. 22, 2012. The entire disclosure of the above-referenced application is incorporated herein by reference.

2. FIELD OF THE INVENTION

The invention relates to an esterification process for the production of a dialkyl-furan-2,5-dicarboxylate (DAFD) vapor in an esterification reactor and subjecting the vapor to rectification.

3. BACKGROUND OF THE INVENTION

Aromatic dicarboxylic acids such as terephthalic acid and isophthalic acid or their di-esters, dimethyl terephthalate as for example, are used to produce a variety of polyester products, important examples of which are poly (ethylene terephthalate) and its copolymers. The aromatic dicarboxylic acids are synthesized by the catalytic oxidation of the corresponding dialkyl aromatic compounds which are obtained from fossil fuels such as those disclosed in US 2006/0205977 A1. Esterification of these diacids using excess alcohol produces the corresponding di-esters has been disclosed in US2010/0210867A1. There is a growing interest in the use of renewable resources as feed stocks for the chemical industries mainly due to the progressive reduction of fossil reserves and their related environmental impacts.

Furan-2,5-dicarboxylic acid ("FDCA") is a versatile intermediate considered as a promising closest biobased alternative to terephthalic acid and isophthalic acid. Like aromatic diacids, FDCA can be condensed with diols such as ethylene glycol to make polyester resins similar to polyethylene terephthalate (PET) as disclosed in Gandini, A.; Silvestre, A. J; Neto, C. P.; Sousa, A. F.; Gomes, M. *J. Poly. Sci. A* 2009, 47, 295. FDCA has been prepared by oxidation of 5-(hydroxymethyl) furfural (5-HMF) under air using homogenous catalysts as disclosed in US2003/0055271 A1 and in Partenheimer, W.; Grushin, V. V. *Adv. Synth. Catal.* 2001, 343, 102-111.

There is a need for a technique for the production, purification, and isolation of esterification products of FDCA and alcohols to make higher purity or higher yield of dialkyl furan dicarboxylates without the necessity for downstream separation of large volumes of high boiling compound intermediates such as 5-(alkoxycarbonyl)furan-2-carboxylic acid.

4. SUMMARY OF THE INVENTION

There is now provided a process for the manufacture of dialkyl furan-2,5-dicarboxylate (DAFD) vapor composition comprising:
a. feeding furan-2,5-dicarboxylic acid ("FDCA") to an esterification reactor; and
b. providing a liquid reaction mixture in the esterification reactor, said liquid reaction mixture comprising FDCA, an alcohol compound, DAFD, water, and 5-(alkoxycarbonyl)furan-2-carboxylic acid (ACFC); and
c. in the presence of said alcohol compound, conducting an esterification reaction in the liquid reaction mixture; and
d. providing an esterification vapor in an esterification vapor space within the esterification reactor above the liquid reaction mixture, said esterification vapor comprising, in vapor form, DAFD, unreacted alcohol compound, ACFC, and water; and
e. continuously passing at least a portion of the esterification vapor into a rectification zone in which at least a portion of the ACFC in the esterification vapor is converted to a liquid phase condensate; and
f. contacting at least a portion of the liquid phase condensate with the liquid reaction mixture; and
g. continuously discharging from the rectification zone a DAFD vapor composition comprising DAFD, water, unreacted alcohol, and by-products.

Desirably the rectification zone is in vapor communication with the esterification vapor, and the rectification zone is either:
(i) enclosed within the hull of the esterification reactor, or
(ii) is mounted on top of the esterification reactor in a manner that condensate developed in the rectification zone flows downward into the esterification vapor space by gravity flow.

There is also provided a vapor composition comprising:
a. at least 10 wt. % alcohol compound;
b. at least 2 wt. % dialkyl furan-2,5-dicarboxylate (DAFD),
c. water;
d. and from zero up to 3 wt. % 5-(alkoxycarbonyl)furan-2-carboxylic acid (ACFC) wherein expressed amounts are based on the weight of the vapor composition.

6. DETAILED DESCRIPTION OF THE INVENTION

It should be understood that the following is not intended to be an exclusive list of defined terms. Other definitions may be provided in the foregoing description, such as, for example, when accompanying the use of a defined term in context.

As used herein, the terms "a," "an," and "the" mean one or more.

As used herein, the term "and/or," when used in a list of two or more items, means that any one of the listed items can be employed by itself or any combination of two or more of the listed items can be employed. For example, if a composition is described as containing components A, B, and/or C, the composition can contain A alone; B alone; C alone; A and B in combination; A and C in combination, B and C in combination; or A, B, and C in combination.

As used herein, the terms "comprising," "comprises," and "comprise" are open-ended transition terms used to transition from a subject recited before the term to one or more elements recited after the term, where the element or elements listed after the transition term are not necessarily the only elements that make up the subject.

As used herein, the terms "having," "has," and "have" have the same open-ended meaning as "comprising," "comprises," and "comprise" provided above.

As used herein, the terms "including," "includes," and "include" have the same open-ended meaning as "comprising," "comprises," and "comprise" provided above.

The present description uses numerical ranges to quantify certain parameters relating to the invention. It should be understood that when numerical ranges are provided, such ranges are to be construed as providing literal support for claim limitations that only recite the lower value of the range as well as claim limitations that only recite the upper value of the range. For example, a disclosed numerical range of 10 to 100 provides literal support for a claim reciting "greater than 10" (with no upper bounds) and a claim reciting "less than 100" (with no lower bounds).

The present description uses specific numerical values to quantify certain parameters relating to the invention, where the specific numerical values are not expressly part of a numerical range. It should be understood that each specific numerical value provided herein is to be construed as providing literal support for a broad, intermediate, and narrow range. The broad range associated with each specific numerical value is the numerical value plus and minus 60 percent of the numerical value, rounded to two significant digits. The intermediate range associated with each specific numerical value is the numerical value plus and minus 30 percent of the numerical value, rounded to two significant digits. The narrow range associated with each specific numerical value is the numerical value plus and minus 15 percent of the numerical value, rounded to two significant digits. For example, if the specification describes a specific temperature of 62° F., such a description provides literal support for a broad numerical range of 25° F. to 99° F. (62° F.+/−37° F.), an intermediate numerical range of 43° F. to 81° F. (62° F.+/−19° F.), and a narrow numerical range of 53° F. to 71° F. (62° F.+/−9° F.). These broad, intermediate, and narrow numerical ranges should be applied not only to the specific values, but should also be applied to differences between these specific values. Thus, if the specification describes a first pressure of 110 psia and a second pressure of 48 psia (a difference of 62 psi), the broad, intermediate, and narrow ranges for the pressure difference between these two streams would be 25 to 99 psi, 43 to 81 psi, and 53 to 71 psi, respectively All references to ppm are by weight on a mass basis.

Figure 1:
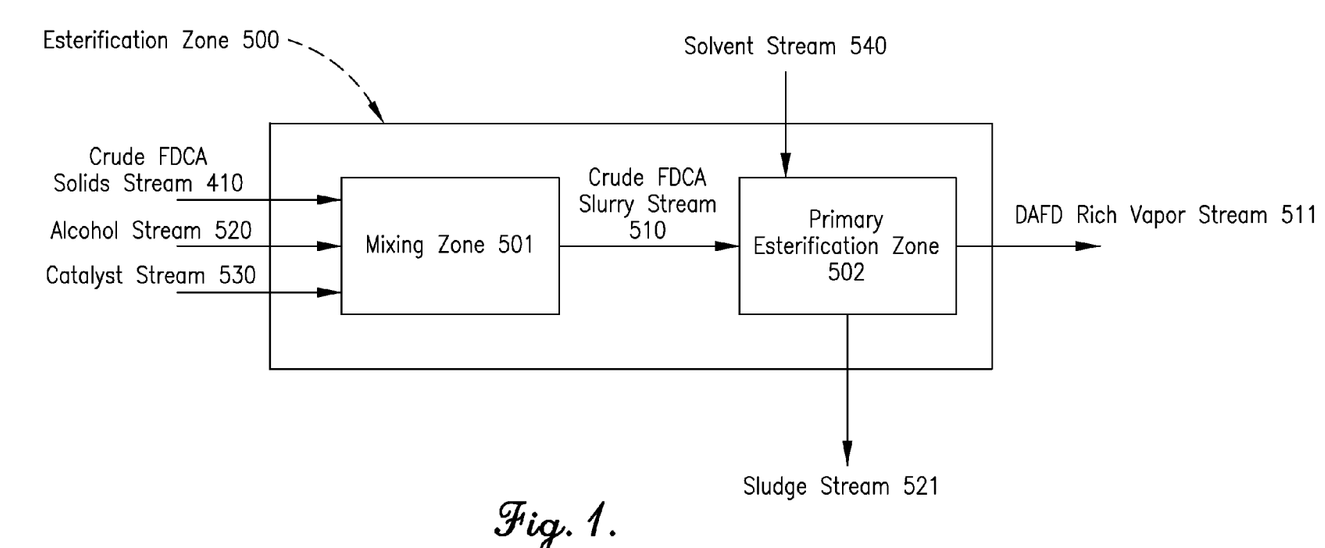
FIG. 1 is a flow diagram of mixing zone and an esterification reactor.

As illustrated in FIG. 1, the crude FDCA solids stream 410, which can be either dried carboxylic acid solids or wet cake or slurry comprising FDCA solids, and the alcohol composition stream 520 are fed to the esterification reaction zone 500. The crude FDCA solids stream 410 can be shipped via truck, ship, or rail as solids. However, an advantage of the invention is that the process for the oxidation of the oxidizable material containing the furan group can be integrated with the process for the manufacture of the DAFD vapor composition. An integrated process includes co-locating the two manufacturing facilities, one for oxidation and the other for esterification, within 10 miles, or within 5 miles, or within 2 miles, or within 1 mile, or within ½ mile of each other. An integrated process also includes having the two manufacturing facilities in solid or fluid communication with each other. If a solid dicarboxylic acid composition is produced, the solids can be conveyed by any suitable means, such as air or belt, to the esterification facility. If a wet cake dicarboxylic acid composition is produced, the wet cake can be moved by belt or pumped as a liquid slurry to the facility for esterification.

FDCA is fed to the esterification zone 500. The esterification zone contains at least an esterification reactor. The esterification reactor contains a liquid reaction mixture. The liquid reaction mixture contains at least FDCA, an alcohol compound, DAFD, water, and 5-(alkoxycarbonyl)furan-2-carboxylic acid (ACFC). An esterification reaction is conducted in the liquid reaction mixture within the esterification reactor 502 at a temperature and pressure effective to react FDCA with the alcohol compound to form an esterification vapor in an esterification vapor space within the esterification reactor above the liquid reaction mixture. The esterification vapor contains, in vapor form, at least DAFD, unreacted alcohol compound, ACFC, and water. Desirably, the primary reaction section in the esterification reactor is within a liquid reaction mixture desirably located at the bottom of the reaction vessel, and by bottom is meant that the liquid reaction mixture contacts the bottom of the internal reaction zone and may have any continuous height from the bottom so long as an esterification vapor space is provided. Although reactions may also occur as further described below between the esterification vapor and falling ACFC condensate, the majority of the reaction occurs in the liquid phase in the liquid reaction mixture contacting the bottom of the esterification vessel.

The alcohol composition comprises one or more types of alcohol compounds. Examples include compounds represented by the structure R—OH wherein R can range from 1 to 6 carbons, or 1 to 5 carbon atoms, or 1 to 4 carbon atoms, or 1 to 3 carbon atoms, or 1 to 2 carbon atoms, preferably methanol. R can be branched or unbranched, saturated or unsaturated, and cyclic or acyclic. Desirably, R is an unbranched, saturated, acyclic alkyl group. The alcohol composition contains at least 50 wt. %, or at least 60 wt %, or at least 70 wt %, or at least 80 wt. %, or at least 90 wt. %, or at least 95 wt %, or at least 97 wt %, or at least 98 wt. %, or at least 99 wt. % alcohol compounds based on the weight of the alcohol composition.

The alcohol is fed to the esterification reactor as a liquid, either as part of the mixed crude FDCA slurry stream 510 or as a separate feed or as a combination of a separate feed and the mixed crude FDCA slurry stream 510. A portion of the alcohol may also be fed to the esterification reactor as a superheated vapor.

As illustrated in FIG. 1, the DAFD vapor composition product stream 511 contains dialkyl furan-2,5-dicarboxylate ("DAFD"), which is the reaction product of at least FDCA with the alcohol compound, where the alkyl moiety is an alkyl group containing 1 to 6 carbon atoms. In the case of a reaction between FDCA and methanol, the diester reaction product comprises dimethyl furan-2,5-dicarboxylate ("DMFD"). The esterification reaction of FDCA with methanol to produce DMFD is a multi-step reaction mechanisms as illustrated below. One mole of FDCA reacts with one mole of an alcohol to produce a mole of 5-(alkoxycarbonyl)furan-2-carboxylic acid (ACFC) and water, or to produce (methoxycarbonyl)furan-2-carboxylic acid (MCFC) and water in the case that the alcohol is methanol. One mole of ACFC can then react with one mole of an alcohol compound to produce one mole of the desired product DAFD and water, or in the case of using methanol in both instances, one mole of MCFC can then react with one mole of methanol to produce DMFD.

Because both DAFD and ACFC are present in an esterification reaction zone, the DAFD vapor composition may also contain some ACFC, depending upon the design of the rectification zone and reaction conditions, in addition to the unreacted alcohol compounds and DAFD.

Esterification by-products formed in the esterification reaction zone can include light boiling compounds: dimethyl ether, methyl acetate, acetaldehyde, and methyl bromide. Other by-products formed in the esterification reaction zone comprise alkyl furan-2-carboxylate (AFC), alkyl 5-formylfuran-2-carboxylate (AFFC), and the ACFC mentioned above. Additional by-products and impurities may be present depending upon the impurities contained within the feedstock feeding an oxidation zone for making FDCA.

It is desirable to first mix the solid FDCA composition or wet cake with the alcohol prior to conducting an esterification reaction under esterification conditions. As illustrated in FIG. 1, there is provided a mixing zone 501 and an esterification zone 502 containing at least one esterification reactor. The crude FDCA solids composition 410 comprising FDCA, and an alcohol composition 520 stream (such as alcohols with 1 to 6 carbon atoms), and optionally an esterification catalyst composition stream 530, are fed to the mixing zone 501 to generate a mixed crude FDCA slurry stream 510 that is the feed to the esterification zone 502.

Mixing in zone 501 may be accomplished by any equipment known in the art for mixing liquid and solids, such as continuous in line static mixers, batch agitated vessels, and or continuous agitated vessels, and the like. The theoretical amount of alcohol required for the reaction with each mole of FDCA. The total amount of alcohol present in mixing zone 501 is desirably in excess of the theoretical amount required for the esterification reaction.

For example, the molar ratio of alcohol to FDCA moles ranges from greater than 2:1, or at least 2.2:1, or at least 2.5:1, or at least 3:1, or at least 4:1, or at least 5:1, or at least 10:1, or at least 15:1, and up to 40:1, or up to 30:1, or up to 20:1, or up to 15:1, or up to 10:1, or up to 8:1, or up to 6:1, or up to 5:1, or up to 4:1, or up to 3:1. Unlike a process in which DAFD product is taken off as a liquid, in this process, it is desired to use smaller molar ratios of alcohol to FDCA in order to produce sludge stream that contains lower quantities of alcohol as a liquid take off from the esterification reactor. Suitable molar ratios are within a range of alcohol to FDCA from greater than 2.0:1, or at least 2.2:1, and up to 15:1, or up to 10:1, or up to 8:1, or up to 6:1, or up to 5:1, or up to 4:1, or up to 3:1.

The esterification catalyst is optional. Since the process is a direct esterification process, and the reaction temperature is high, the direct esterification reaction can proceed in the absence of a catalyst. However, an esterification catalyst can be added if desired. The catalyst is can be heterogeneous in a fixed bed or desirably a homogenous catalyst under esterification reaction conditions, and can also be homogeneous in the mixing zone. Known organometallic esterification catalysts can be used such as the acetate of cobalt, copper and manganese, and zinc in amounts conventionally used for esterifying terephathalic acid. Other organic catalysts can be employed such as sulfuric acid, tosylic acid, and Lewis acids.

The crude FDCA slurry stream 510 is routed to esterification reactor 502 to form part of the liquid reaction mixture. The crude FDCA slurry stream can be fed into the esterification reactor at a rate corresponding to a desired throughput in a continuous process for the production of a vapor DAFD composition. Examples of suitable rates for the production of a DAFD vapor composition stream include an average of at least 1000 kg/day, or at least 10,000 kg/day, or at least 20,000 kg/day, or at least 50,000 kg/day, or at least 75,000 kg/day, or at least 100,000 kg/day, or at least 200,000 kg/day of a DAFD vapor composition, on a 24 hour basis over the course of any three months.

The process can be conducted batchwise, semi-batch wise, or continuously. It is desirable to form a condensate of ACFC continuously, or it is desirable to remove the esterification vapor continuously. It is desirable to conduct the whole process on a continuous basis.

The liquid reaction mixture comprises FDCA, the alcohol compound, the reaction product DAFD, water, and ACFC. It may also contain AFC, AFFC, and optionally the rectification solvent and esterification catalyst. The liquid reaction mixture optionally contains solids of FDCA that over the course of the reaction solubilize in the liquid phase. On a continuous basis, the liquid reaction mixture may simultaneously dissolve solids and contain solids of FDCA since fresh undissolved solids of FDCA are continuously fed into the reaction mixture while simultaneously dissolving FDCA solids in the liquid reaction mixture.

The process conditions within the esterification reactor both generate the DAFD product and vaporize the DAFD product into an esterification vapor in a vapor space within the esterification reactor above the liquid level of the reaction mixture. The esterification vapor in the esterification reactor contains vaporized components of DAFD, alcohol, water, and ACFC. The DAFD vapor composition that has exited the rectification zone contains at least DAFD and unreacted alcohol compounds.

Desirably, DAFD is present in the DAFD vapor composition in an amount of at least 1 wt. %, or at least 2 wt. %, or at least 5 wt. %, or at least 7 wt. %, or at least 8 wt. %, or at least 10 wt. %, or at least 15 wt. %, or at least 25 wt. %, or at least 35 wt %, based on the weight of the DAFD vapor composition.

Desirably, weight ratio of the quantity of DAFD present in the DAFD vapor stream composition 510 to the quantity of DAFD present in the sludge composition stream 521 is at least 50:1, or at least 100:1, or at least 150:1, or at least 200:1, or at least 250:1, or at least 300:1.

The concentration of alcohol in the DAFD vapor composition is at least 1 wt. %, or at least 2 wt. %, or at least 3 wt. %, and up to 95 wt. %, or up to 50 wt. %, or up to 25 wt. %, or up to 20 wt. %, or up to 15 wt. %, or up to 10 wt. %, each based on the weight of the DAFD vapor composition. If a rectification solvent is used, it is desired that the concentration of alcohol in the DAFD vapor composition is up to 45 wt. %, or up to 40 wt. %, or up to 35 wt. %, up to 20 wt. %, or up to 15 wt. %, or up to 10 wt. %.

Some of the ACFC compounds in the esterification vapor may not condense and may be present in the DAFD vapor composition. The process of the invention minimizes the amount of ACFC present in the DAFD vapor composition relative to the amount of DAFD present in the DAFD vapor composition by condensing at least a portion of the ACFC from the esterification vapor. The weight ratio of ACFC in the DAFD rich composition relative to the weight of DAFD in the DAFD rich composition is desirably less than 0.5:1, or less than 0.1:1, or less than 0.05:1, or less than 0.02:1.

The yield of DAFD in the DAFD vapor composition is desirably high. Suitable yields are at least 55 mole %, or at least 60 mole %, or at least 65%, or at least 70 mole %, or at least 75 mole %, or at least 80 mole %, or at least 85 mole %, or at least 90 mole %, or at least 95 mole %, or at least 99 mole %. The yield of DAFD in the DAFD vapor composition is calculated as follows:

(mol of DAFD in the DAFD vapor stream composition/starting mol of FDCA)*100%.

Esterification may be accomplished in batch or continuous reactors and comprises one or multiple reaction vessels that are capable of providing acceptable reaction residence time, temperature, and pressure. The esterification reaction residence time ranges from 0.5 hr to about 10 hours.

The esterification temperature of the reaction mixture is effective to vaporize the DAFD in the esterification reactor under operating conditions. Desirably, the reaction mixture is at or above the critical temperature of the alcohol selected to help with mass transfer into the rectification zone. Suitable reaction temperatures range from 150° C. to 400° C., or from 200° C. to 310° C., or from 200° C. to 300° C., or from 200° C. to 290° C., or from 220° C. to 285° C., or from 230° C. to 285° C. or from 230° C. to 280° C. or from 230° C. to 270° C. or from or from 239° C. to 300° C. or from 239° C. to 285° C., or from 239° C. to 260° C. Desirably, the esterification temperature is effective, with all other operating and feed conditions, to evaporate DAFD, unreacted alcohol, rectification solvent, and water but desirably and preferably is not be so high as to degrade DAFD into by-products in undesirable quantities. Desirably, the reaction temperature should be at or above the super-critical temperature of the alcohol reactant to improve the mass transfer rates and diffusivity of alcohol in the reaction mixture. The particular reaction temperature selected will also be dependent upon the pressure conditions within the esterification reactor, if and what kind of esterification catalyst is employed, and if and the kind of rectification solvent used and its feed rate.

The esterification pressure within the esterification reactor and esterification reactor, or the pressure at which the esterification vapor is formed, is desirably at least 1 psia, or at least 5 psia, or at least or more than 14.696 psia, or at least 20 psia, or at least 30 psia, or at least 50 psia, or at least 60 psia, or at least 80 psia, and in each case up to 300 psia, or up to 250 psia, or up to 200 psia, or up to 150 psia, or up to 125 psia. The particular temperature and pressure selected is effective to vaporize DAFD within the esterification reactor such that DAFD exits the esterification reactor as a vapor. Keeping a super-atmospheric pressure (i.e. above 14.696 psia) within the esterification reactor is beneficial to keep the alcohol in liquid phase for a time sufficient to allow it to react in the liquid reaction mixture with FDCA. Lower pressures allow one to drop the reaction temperature and thereby reduce by-product formation or DAFD degradation.

In the course of the esterification reaction between the alcohol and FDCA, DAFD and the monoester ACFC are formed in the esterification reactor as shown in the reaction equations above. Additionally, as FCDA is fed to the primary esterification reaction zone 502 as a crude FDCA slurry stream 510 or directly without first premixing in mixing zone 501, it fuels the formation of ACFC by reacting with the product DAFD to form the half ester ACFC, which in turn reacts with an alcohol to form more DAFD.

However, it is desired to minimize the amount of ACFC that is contained in the DAFD vapor stream taken from the esterification reactor to increase the quantity and yield of DAFD product in the DAFD vapor stream while also reducing the amount of ACFC in that stream which has the benefit of reducing the mass of ACFC that must be separated from the DAFD vapor stream downstream. Merely taking off the esterification vapor from the esterification vapor space without treatment prior to feeding a first separation apparatus (other than the rectification zone) will result in a DAFD vapor stream that contains unnecessarily large quantities of ACFC. This is the case even when the reaction mixture temperature is below the normal boiling point of ACFC. For example, while the boiling point of MCFC (estimated at 346° C.) is significantly higher than the boiling point of DMFD (estimated at 281° C.), nevertheless significant quantities of ACFC can vaporize into the esterification vapor, even though the reaction mixture temperature is below the normal boiling point of ACFC, because of the mass transfer effect as the alcohol or solvent gas bubbles pass through the liquid phase of the reaction mixture in the esterification reactor stripping a portion of the ACFC from the liquid phase. Without treating this esterification vapor in the primary esterification zone 502, substantially all of the ACFC vaporized would be found in DAFD vapor rich stream.

To reduce the amount of ACFC flowing out of the esterification zone 502 into the DAFD vapor stream 511 discharged from this zone, the esterification vapor generated in the esterification reactor passes through a rectification zone prior to exiting the esterification reaction zone 502. In the rectification zone, at least a portion of the ACFC in the esterification vapor is converted to a liquid phase ACFC condensate. The rectification zone can be a rectification zone or a simple heat exchange zone.

The rectification zone is optionally but desirably integral with the esterification reactor. By "integral" is meant that the rectification zone is in vapor communication with the esterification vapor and is either contained within the hull of the esterification vessel or is a separate vessel in vertically orientation with the esterification vessel (e.g., mounted on top of the esterification vessel) such that the condensate developed in the rectification zone falls by gravity flow vertically downward into the liquid reaction mixture within the esterification reactor, either directly through the esterification vapor or indirectly avoiding the esterification vapor. By vertical is meant a drop that is in vertical orientation between a commencing point and the liquid reaction mixture destination, where the commencing point is at the first tray, or bottom of packing, or bottom of a heat exchanger (in closest proximity to the liquid reaction mixture) and the liquid reaction mixture destination can be anywhere in the liquid reaction mixture. Thus, the condensate may fall by gravity directly vertically into the liquid reaction mixture or may flow through a path that includes horizontal pathways or any other orientation other than vertical so long as the liquid reaction mixture destination is in vertical orientation to the rectification zone. Such vertical orientation can be skewed or in alignment.

Figure 2:
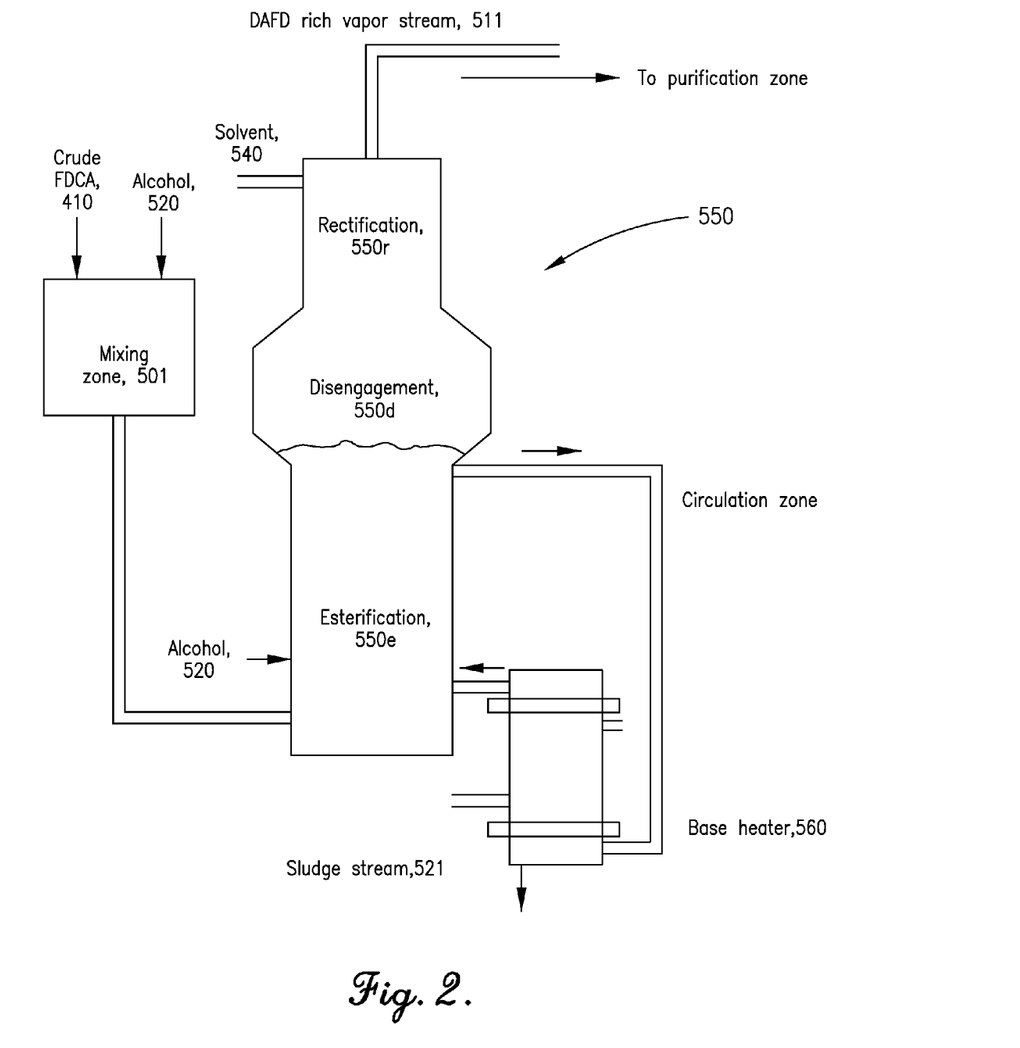
FIG. 2 is a diagram of an esterification reactor containing a rectification zone enclosed by the esterification reactor.

The fabrication method and design in not particularly limited. As shown in FIG. 2, the ACFC zone can be enclosed within the esterification reactor; that is, within the hull or mechanically integrated with the walls or interior of the esterification reactor. Crude FDCA solids stream 410 is fed into the mixing zone 501 along with the alcohol stream 520 to produce a crude FDCA slurry 510 fed into the esterification reactor 550 within zone 502. The esterification reactor 550 in this embodiment contains an esterification zone 550e, and disengagement zone 550d, and a rectification zone 550r. The zones 550e, 550d, and 550r are within the hull of the esterification reactor 550 or integral with hull of the esterification reactor 550. The rectification zone 550r, disengagement zone 550d, and esterification zone 550e can each be flanged together with bolts, welded to 550e, fabricated as a uniform single continuous vessel, or a combination of each. A rectification solvent 540 is fed into the rectification zone. The DAFD vapor stream 511 is discharged from the esterification reactor as a vapor. A portion of the liquid reaction mixture is discharged from the esterification reactor vessel to circulate through a base heater 560 to heat the liquid reaction mixture and fed back into the base of the esterification reactor 550. The rectification zone that is integral with the esterification reactor is desirably also in fluid communication with the esterification vapor space so that condensate developed in the rectification zone is directed from the rectification zone into the liquid reaction mixture within the esterification reactor. Preferably, the condensate developed in the rectification zone flows into the esterification vapor space by a falling action driven by gravity.

Figure 3:
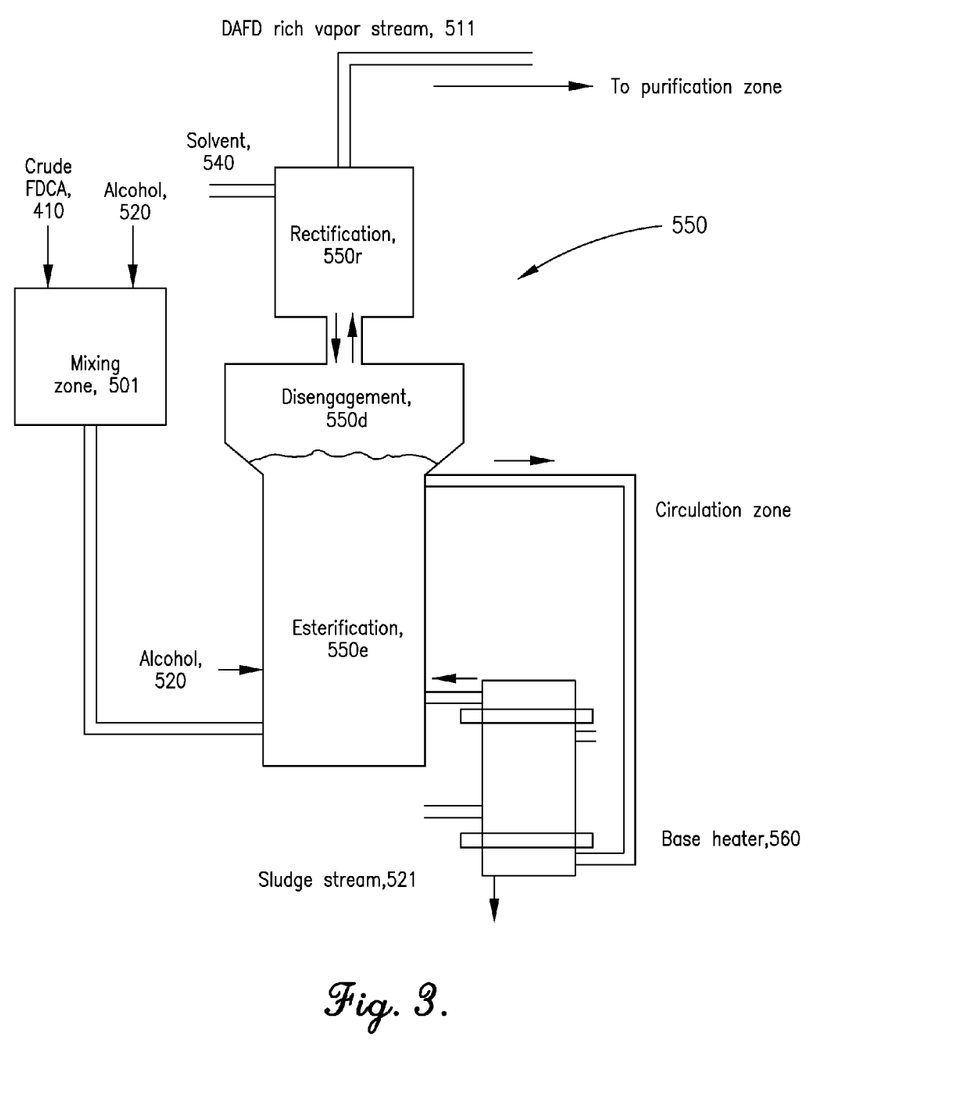
FIG. 3 is a diagram of an esterification reactor to which is mounted a distillation column on top and in mechanical communication with the outlet of the esterification reactor.

Alternatively, as shown in FIG. 3, the rectification zone 550r can be in mechanical communication with the disengagement zone 550d through a pipe 550p such that the esterification vapor is in vertical orientation with the rectification vessel 550r. Preferably, the condensate developed in the rectification zone flows into the esterification vapor space by a falling action driven by gravity. Thus, although a pipe may connect the disengagement zone 550d outlet to the inlet of the rectification zone, the configuration should be one such that the condensate can fall from the rectification zone back into the esterification reactor vertically and be capable of being fed into the disengagement zone by gravity. To be in vertical orientation, the bottom of the rectification vessel must be above the horizontal plane of the top of the liquid reaction mixture liquid level. Accordingly, the rectification zone 550r can be in vertical orientation with the disengagement zone 550d even though the two vessels are not vertically aligned along the same vertical center line. The two vessels can be skewed from each along a horizontal plane.

In certain embodiments, not illustrated, the rectification zone 550r is not integral with the esterification zone and is not in vertical orientation with esterification reactor 550r but nevertheless the rectification vessel 550r is in vapor communication with the disengagement zone 550d. The rectification zone can be a stand-alone unit operation that is not vertically oriented with the liquid reaction mixture. In this embodiment, the bottom of the disengagement vessel 550 is below the top of the reaction mixture liquid level within the esterification zone 550e.

In a rectification zone, if a rectification solvent is used, the esterification vapor and a liquid rectification solvent stream 540 introduced into the rectification zone are passed countercurrent to one another through a rectification column having multiple points of contact between the esterification vapor and the esterification liquid solvent. The countercurrent movement of the vapor and liquid phases follows both heat and mass exchanges at each contact stage until the phases are in equilibrium. The ascending flow of esterification vapor is continuously enriched with compounds more volatile than ACFC, while the descending flow of liquid rectification solvent is enriched with ACFC and any other compounds less volatile than ACFC. As the esterification vapors pass through said rectification section, some vapors are condensed in the rectification zone and flow back into the esterification vapor space as a condensate. Some of the condensate will vaporize before contacting the reaction mixture and some of the condensate will contact the liquid reaction mixture before it is again vaporized.

The rectification zone process conditions are designed to condense a portion of ACFC compounds in the esterification vapor. The condensate desirably contains at least 0.5 wt. % ACFC, or at least 1 wt. % ACFC, or at least 1.5 wt. % ACFC, and can be as high as 25 wt. %, or as high as 20 wt. %, or as high as 15 wt. %. The rectification zone will likely also condense some DAFD. The concentration of ACFC declines as one condenses more of the esterification vapor since more DAFD condenses as the condensation conditions become more severe. One many allow more DAFD to remain in the vapor state to thereby increase the concentration of ACFC in the condensate, however, by so doing, more ACFC will have to be separated downstream since a higher proportion of ACFC will also remain in the vapor state, leaving less ACFC available to further react with DAFD in the liquid reaction mixture. To make more ACFC available for further reaction with the liquid reaction mixture, it is desired to condense a higher amount of ACFC from the esterification vapor, and by so doing, the concentration of ACFC will be on the lower side; for example, up to 5 wt. %, or up to 4 wt. %, or up to 3 wt. %, although the mass of ACFC recovered through condensation will be higher.

If the rectification zone is a rectification zone, it can comprise distillation trays, packing, a spray region, or other method known in the art for condense a vapor. A suitable number of distillation trays ranges from 2 to 30 actual trays, and 2 to 25 trays are sufficient to condense ACFD compounds. The actual tray configuration is not limited, and can include bubble trays, perforated trays, dual flow trays, or even baffles. A sharp separation between ACFC and the esterification vapor is not needed. By a sharp separation is meant a substantially complete removal of ACFC from the esterification vapor. While it is desired to recover a large percentage of ACFC from the esterification vapor (e.g. greater than 50%, or greater than 60%, or at least 70%, or at least 80%, or at least 90%, or at least 95%, or at least 97%, or at least 98%, or even at least 99%), it is not essential to do so, although lower amounts of ACFC recovery results in a larger volume of ACFC in the vapor product stream that will have to be separate downstream and recycled, and lowers the yield of DAFD because not all of the ACFC may be recoverable downstream for recycle and leaves more opportunity for ACFC to react downstream to form other by-products.

The number of trays selected will depend upon the desired recovery of ACFC, and the amount of rectification solvent fed into the rectification zone. If a rectification solvent is used, the feed rate is not particularly limited. Since a sharp separation of ACFC from the esterification vapor is not required, the process of the invention is robust enough to allow for low or high rectification solvent feed rates. Suitable rectification solvent feed rates as a mass ratio of rectification solvent composition to the mass of FDCA feed include at least 0.50 kg solvent per kg of FDCA fed, or at least 1 kg/kg, or at least 1.5 kg/kg, or at least 2 kg/kg, or at least 2.5 kg/kg, or at least 3 kg/kg, and up to about 10 kg/kg, or up to about 8 kg/kg, and up to about 7 kg/kg, and up to about 6.5 kg/kg. An excess of rectification solvent fed can increase the efficiency of the recovery of esterification vapor so much that an undesirably amount of DAFD product is also recovered, while very low amount of rectification solvent fed can result in loss of efficiency and an undesirable amount of ACFC remains in vapor state and is discharged from the esterification zone. The amount of rectification solvent fed is dependent upon the desired capital expenditure to install trays and the desired efficiency of recovery of ACFC without an excessive recovery of DAFD product. However, as previously mentioned, the presence of a rectification solvent is optional as is the presence of trays or packing. If one desires a high rate of recovery of ACFC while minimizing the amount of DAFD recovered, one may employ a solvent feed rate of about at least 0.9 kg/kg up to 6 kg/kg with 5 to 25 trays, or 10 to 25 trays, to obtain an ACFC recovery in excess of 90%, and in some cases in excess of 97%, or at least 98%, or even at least 99%. It is understood that anytime trays are mentioned, packing can be used instead of or in addition to trays in an amount or volume to establish equivalent separation efficiencies.

Instead of distillation trays, the rectification zone can be configured with baffles or packing material (e.g. Raschig rings), such as random dumped packing within the rectification zone, or structured metal packing.

An advantage of the invention is that a condenser is not required. The rectification zone is desirably equipped without reflux; rather a feed of rectification solvent is fed into the rectification zone wherein the esterification solvent is not obtained by refluxing the esterification vapor. The esterification solvent may be recovered from the DAFD vapor product by separation and distillation, and then recycled back to the rectification zone.

The residence time of FDCA and DAFD in the esterification reactor is effective to form DAFD, vaporize DAFD, and produce a vaporized effluent comprising DAFD. Suitable average residence times run from 5 seconds to 1 hour. The reaction rate between FDCA and the alcohol is quick, and at the reaction temperatures and flow rate of feeds into the esterification reactor, the ingredients vaporize quickly. Thus, the process is capable of short average residence times ranging from 5 seconds to 5 minutes, or 30 seconds to 5 minutes.

To assist with the formation of condensate, a rectification solvent stream 540 can be fed to the rectification zone. The rectification solvent stream 540 desirably moves in a countercurrent direction to the esterification vapor. The rectification solvent stream preferably flows downwardly with the force of gravity. The rectification solvent is desirably introduced as a liquid into the rectification zone. It can be introduced at the top of the rectification zone such that the liquid contacts the uppermost tray or packing surface, or is introduced as a spray reflux in the top ⅙ rectification zone height. The liquid rectification solvent can also be introduced at other points across the rectification zone to ensure the presence of liquid rectification solvent throughout the rectification zone trays or packing.

The flow of rectification solvent stream cools the esterification vapor and condenses the high boiling point compounds, such as ACFC compounds. It is desired that at least 25%, or at least 50%, or at least 75%, or at least 90% of the ACFC vapor entering the rectification zone is condensed in the rectification zone and prevented from exiting the primary esterification reaction zone or in the DAFD vapor stream 511. The purpose for condensing a portion of the ACFC vapor in the rectification section is to prevent said portion of ACFC from exiting esterification reactor 502, thereby providing additional residence time for that portion of ACFC to react with methanol in the esterification reactor to form the desired product DAFD. Since ACFC is an intermediate mono-ester, it can further react with the alcohol to produce the desired DAFD product. The reaction between the condensed ACFC and alcohol can occur in the liquid reaction mixture, or in the esterification vapor space as liquid ACFC contacts vaporous alcohol during its descent into the liquid reaction mixture, or in the esterification vapor space as some condensate vaporizes to cause a reaction between vaporous ACFD and vaporous alcohol, or a reaction in a combination of all three physical states.

The process of the invention is also robust because the possible entrainment of small amounts of DAFD vaporized compounds into the downward rectification solvent stream flow can beneficially fuel the production of yet more DAFD product. As shown in the reaction scheme above when methanol is used as the alcohol, one mole of entrained DMFD taken out of the esterification vapor stream can react with a mole of FDCA in the reaction mixture to generate two moles of MCFC, which in turn can react with two moles of methanol to produce two moles of DAFD, which in turn vaporizes.

The rectification solvent stream 540 desirably is inert to FDCA and DAFD and ACFC. It also is desirably selected to have a boiling point below the boiling point of AFC in order to make downstream separation by distillation more efficient. Other more preferred selection criteria for the rectification solvent is one that is easily separated from alcohol, does not azeotrope with the alcohol employed in the reaction mixture, has a melting point below 20° C., and is reaction heat stable. An example of a suitable rectification solvent is ortho, meta, and para-xylene, preferably a solvent containing at least 25 wt. % o-xylene.

The rectification solvent stream can be a reflux or can be a continuous feed of fresh solvent. As a reflux, it is desired that the source of the recycled solvent stream is distillate taken from the DAFD vapor stream or other downstream feeds to one or more distillation columns. Once introduced into the esterification reactor, the rectification solvent is not separated from the esterification vapor until after the esterification vapor has passed through the rectification zone.

As mentioned above, the DAFD vapor composition, after having passed through a rectification zone, comprises DAFD, unreacted alcohol compound, water, and ACFC; and if used, a rectification solvent and a homogeneous esterification catalyst. Thus, there is now also provided a DAFD vapor composition comprising, where any expressed amounts are based on the weight of the vapor composition:

an alcohol compound,
at least 1 wt. % dialkyl furan-2,5-dicarboxylate (DAFD), water,
5-(alkoxycarbonyl)furan-2-carboxylic acid (ACFC),
alkyl furan-2-carboxylate (AFC), and
alkyl 5-formylfuran-2-carboxylate (AFFC).

The composition of the DAFD vapor stream can also comprise the following compounds in the gaseous state, expressed as a concentration by weight based on the weight of the DAFD vapor stream:

DAFD: at least 1 wt. %, or at least 2 wt. %, or at least 3 wt. %, and up to 95 wt. %, or up to 50 wt. %, or up to 40 wt. %;

ACFC: from zero, or at least greater than zero, and up to 3 wt. %, or up to 2 wt. %, or up to 1 wt. %, or up to 1000 ppm, or up to 100 ppm;

alcohol: from at least 1 wt. %, or at least 5 wt. %, or at least 10 wt. %, or at least 15 wt. %, and up to 80 wt. %, or up to 50 wt. %, or up to 30 wt. %;

water: from at least 0.5 wt. %, or at least 1 wt. %, or at least 1.5 wt. %, or at least 2 wt. %, or at least 4 wt. %, or at least 5 wt. %, and up to 20 wt. %, or up to 15 wt. %, or up to 10 wt. %, or up to 8 wt. %;

AFC: from at least 0.5 wt. %, or at least 1 wt. %, and up to 10 wt. %, or up to 8 wt. %, or up to 6 wt. %, or up to 5 wt. %, or up to 4 wt. %;

AFFC: from at least 0.01 wt. %, or at least 0.1 wt. %, or at least 0.3 wt. %, and up to 3 wt. %, or up to 2 wt. %, or up to 1 wt. %; and optionally rectification solvent: from at least zero, or at least greater than 0, or at least 1 wt. %, or at least 2 wt. %, or at least 5 wt. %, and up to 45 wt. %, or up to 40 wt. %;

The molar ratio of ACFD to DAFD in the DAFD vapor composition is not particularly limited, but advantageously the molar ratio is small to take advantage of reacting the half ester ACFC further to improve the yield of DAFD. For example, the molar ratio of ACFC to DAFD is not greater than 0.2:1, or not greater than 0.1:1, or not greater than 0.08:1, or not greater than 0.06:1, or not greater than 0.05:1, or not greater than 0.04:1, or not greater than 0.02:1, or not greater than 0.01:1, or not greater than 0.008:1, or not greater than 0.006:1, or not greater than 0.005:1, or not greater than 0.003:1, or not greater than 0.002:1, or not greater than 0.001:1.

The rectification solvent is separated after the esterification vapor is discharged from the outlet or top of the rectification zone, or rectifier column if one is used. Desirably, the rectification solvent is separated after or with the separation of the alcohol from the DAFD vapor composition.

The flow rate of such a DAFD vapor stream can be at least 1,000 kg/day, or at least 3,000 kg/day, or at least 5,000 kg/day, or at least 10,000 kg/day, or at least 20,000 kg/day, or at least 50,000 kg/day, or at least 75,000 kg/day, or at least 100,000 kg/day, or at least 200,000 kg/day, or at least 400,000 kg/day, or at least 500,000 kg/day, on a 24 hour basis over the course of any three months. The flow rate of DAFD product within the DAFD vapor stream can be at least 500 kg/day, or at least 1500 kg/day, or at least 3,000 kg/day, or at least 5,000 kg/day, or at least 10,000 kg/day, or at least 25,000 kg/day, or at least 40,000 kg/day, or at least 50,000 kg/day, or at least 100,000 kg/day, or at least 200,000 kg/day, or at least 400,000 kg/day, on a 24 hour basis over the course of any three months.

The DAFD vapor stream can be condensed downstream and through a sequence of distillation column, further purified to isolate DAFD as a molten liquid or a solid powder.

As illustrated in FIG. 1, a sludge stream 521 comprising high boilers present in primary esterification reactor is discharged from esterification zone 500. The majority of DAFD made in the liquid phase reaction mixture is vaporized. The sludge stream 521 is a liquid discharged from the esterification reactor. It can be one or more liquid streams discharged from the esterification reactor. It may contain some solids such as undissolved FDCA. The sludge stream typically comprises ACFC and DAFD and unreacted FDCA. The mass ratio of DAFD in the DAFD vapor stream relative to mass of DAFD in the sludge stream on a kg:kg basis is at least 90:1, or at least 95:1, or at least 98:1, or at least 99:1, or at least 99.3:1, or at least 99.5:1, or at least 99.8:1, or at least 99.9:1, or at least 99.95:1. For purposes of this calculation, the sludge stream is deemed to be the cumulative amount of all liquid streams discharged from the esterification reactor, and the mass of the solids in such streams are considered in the mass of the sludge stream calculation.

The mode of operation can be illustrated by the following example which is a model designed in ASPEN.

45,146 kg/day of crude FDCA is fed as solid stream 410 into mixing zone 501 along with 44,707 kg/day of liquid methanol stream 520. 45,146 kg/day of rectification solvent stream 540 comprising o-xylene is fed to the top tray of the rectification zone 550r of an esterification reactor 550 in which the rectification zone 550r is integral with the esterification reactor 550 as shown in FIG. 2. The rectification zone 550r contains 25 trays. An additional 8,941 kg/day of superheated methanol vapor stream 520sh as a stripping agent is fed to a slipstream discharged from the base heater to produce 996 kg/day of sludge stream 521. The liquid reaction mixture is allowed to react within the esterification reaction zone 550e at a temperature of about 240° C. and a pressure of 20 psia. The DMFD rich vapor stream 511 consists of 50,000 kg/day of DMFD; 35,285 kg/day of methanol; 10,435 kg/day of water; 42,889 kg/day of o-xylene; 2,740 kg/day of MFC; 1,412 kg/day of MFFC; and 91 kg/day of MCFC, with the remainder being other by-products and impurities, for a total stream mass of 142,944 kg/day.

The FDCA composition fed to the esterification reactor is not particularly limited. However, the FDCA composition is desirably made according to the following process.

The process comprises feeding an oxidizable composition to an oxidation zone, where the oxidizable composition contains a compound having a furan moeity. The furan moiety can be represented by the structure:

The compounds having a furan moiety are such that, upon oxidation, form carboxylic acid functional groups on the compound. Examples of compounds having furnan moieties include 5-(hydroxymethyl)furfural (5-HMF), and derivatives of 5-HMF. Such derivatives include esters of 5-HMF, such as those represented by the formula 5-R(CO)OCH$_2$-furfural where R=alkyl, cycloalkyl and aryl groups having from 1 to 8 carbon atoms, or 1-4 carbon atoms or 1-2 carbon atoms; ethers of 5-HMF represented by the formula 5-R'OCH$_2$-furfural, where R'=alkyl, cycloalkyl and aryl having from 1 to 8 carbon atoms, or 1-4 carbon atoms or 1-2 carbon atoms); 5-alkyl furfurals represented by the formula 5-R"-furfural, where R"=alkyl, cycloalkyl and aryl having from 1 to 8 carbon atoms, or 1-4 carbon atoms or 1-2 carbon atoms). Thus the oxidizable composition can contain mixtures of 5-HMF and 5-HMF esters; 5-HMF and 5-HMF ethers; 5-HMF and 5-alkyl furfurals, or mixtures of 5-HMF and its esters, ethers, and alkyl derivatives.

The oxidizable composition, in addition to 5-(hydroxymethyl)furfural (5-HMF) or an of its derivatives, may also contain 5-(acetoxymethyl)furfural (5-AMF) and 5-(ethoxymethyl)furfural (5-EMF).

Figure 4:
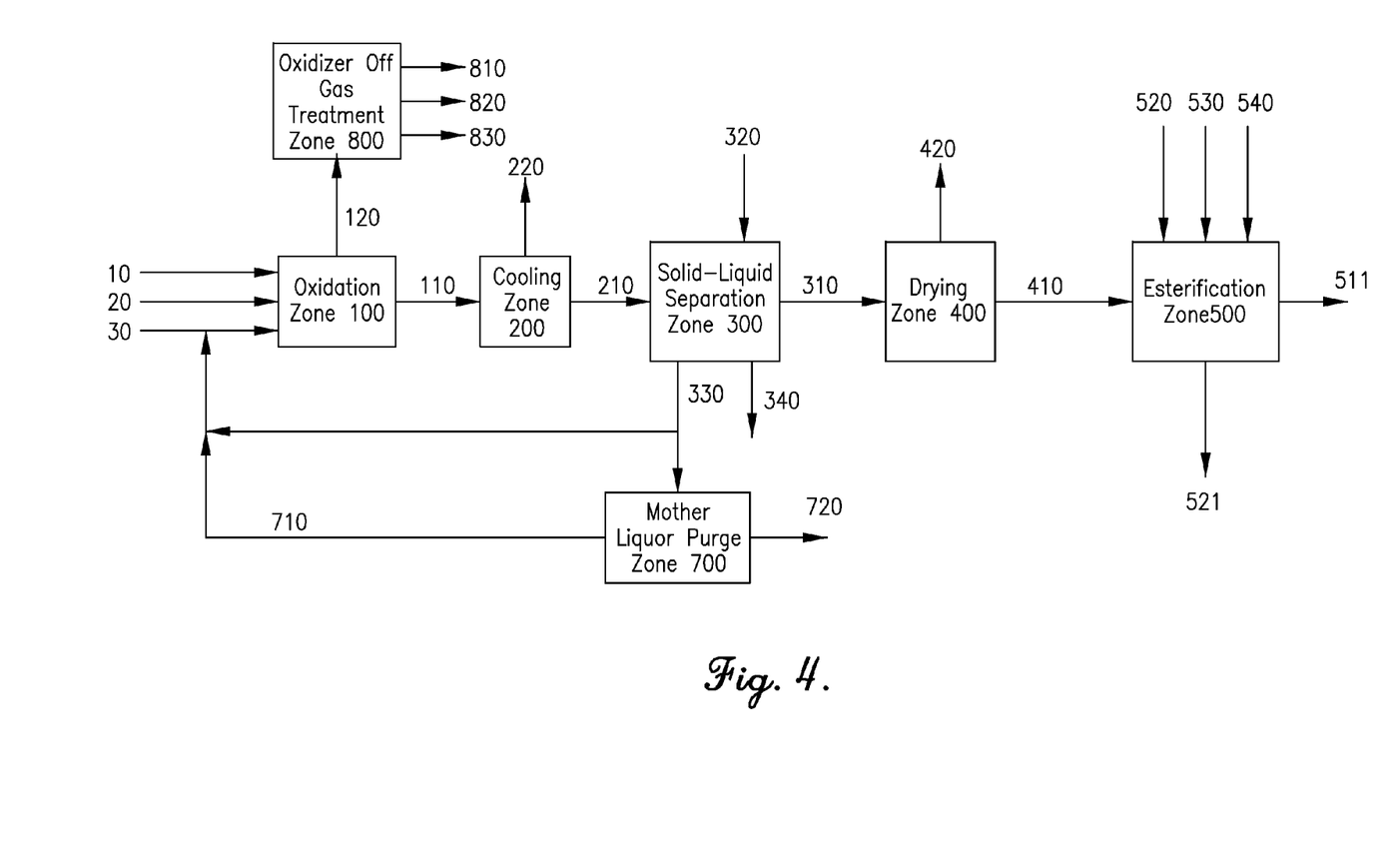
FIG. 4 is a flow diagram illustrating the manufacture of FDCA and its subsequent purification.

Specific examples of 5-HMF derivatives include those having the following structures:

Preferred 5-HMF Derivative Feeds 5-methoxymethylfurfural
5-formoxymethylfurfural
5-methylfurfural
5-ethoxymethylfurfural
5-acetoxymethylfurfural
5-propoxymethylfurfural
5-propionoxymethylfurfural
5-butoxymethylfurfural
5-butyroxymethylfurfural One embodiment is illustrated in FIG. 4. An oxidizable composition is fed to a primary oxidation zone 100 and reacted in the presence of a solvent, a catalyst system, and a gas comprising oxygen, to generate a crude dicarboxylic acid stream 110 comprising furan-2,5-dicarboxylic acid (FDCA).

For example, the oxidizable composition containing 5-HMF, or its derivatives, or combinations thereof, are oxidized with elemental $O_2$ in a multi-step reaction to form FDCA with 5-formyl furan-2-carboxylic acid (FFCA) as a key intermediate, represented by the following sequence:

If desired, the oxygen gas stream 10 comprising oxygen, a solvent stream 30, and the oxidizable stream 20 can be fed to the primary oxidation zone 100 as separate streams. Or, an oxygen stream 10 comprising oxygen as one stream and an oxidizable stream 20 comprising solvent, catalyst, and oxidizable compounds as a second stream can be fed to the primary oxidation zone 100. Accordingly, the solvent, oxygen gas comprising oxygen, catalyst system, and oxidizable compounds can be fed to the primary oxidization zone 100 as separate and individual streams or combined in any combination prior to entering the primary oxidization zone 100 wherein these feed streams may enter at a single location or in multiple locations into the primary oxidizer zone 100.

The catalyst can be a homogenous catalyst soluble in the solvent or a heterogeneous catalyst. The catalyst composition is desirably soluble in the solvent under reaction conditions, or it is soluble in the reactants fed to the oxidation zone. Preferably, the catalyst composition is soluble in the solvent at 40° C. and 1 atm, and is soluble in the solvent under the reaction conditions.

Suitable catalysts components comprise at least one selected from, but are not limited to, cobalt, bromine and manganese compounds. Preferably a homogeneous catalyst system is selected. The preferred catalyst system comprises cobalt, manganese and bromine.

The cobalt atoms may be provided in ionic form as inorganic cobalt salts, such as cobalt bromide, cobalt nitrate, or cobalt chloride, or organic cobalt compounds such as cobalt salts of aliphatic or aromatic acids having 2-22 carbon atoms, including cobalt acetate, cobalt octanoate, cobalt benzoate, cobalt acetylacetonate, and cobalt naphthalate. The oxidation state of cobalt when added as a compound to the reaction mixture is not limited, and includes both the +2 and +3 oxidation states.

The manganese atoms may be provided as one or more inorganic manganese salts, such as manganese borates, manganese halides, manganese nitrates, or organometallic manganese compounds such as the manganese salts of lower aliphatic carboxylic acids, including manganese acetate, and manganese salts of beta-diketonates, including manganese acetylacetonate.

The bromine component may be added as elemental bromine, in combined form, or as an anion. Suitable sources of bromine include hydrobromic acid, sodium bromide, ammonium bromide, potassium bromide, and tetrabromoethane. Hydrobromic acid, or sodium bromide may be preferred bromine sources.

The amount of bromine atoms desirably ranges from at least 300 ppm, or at least 2000 ppm, or at least 2500 ppm, or at least 3000 ppm, or at least 3500 ppm, or at least 3750, ppm and up to 4500 ppm, or up to 4000 ppm, based on the weight of the liquid in the reaction medium of the primary oxidation zone. Bromine present in the an amount of 2500 ppm to 4000 ppm, or 3000 ppm to 4000 ppm are especially desirable to promote high yield.

The amount of cobalt atoms can range from at least 500 ppm, or at least 1500 ppm, or at least 2000 ppm, or at least 2500 ppm, or at least 3000 ppm, and up to 6000 ppm, or up to 5500 ppm, or up to 5000 ppm, based on the weight of the liquid in the reaction medium of the primary oxidation zone. Cobalt present in an amount of 2000 to 6000 ppm, or 2000 to 5000 ppm are especially desirable to promote high yield.

The amount of manganese atoms can range from 2 ppm, or at least 10 ppm, or at least 30 ppm, or at least 50 ppm, or at least 70 ppm, or at least 100 ppm, and in each case up to 600 ppm, or up to 500 ppm or up to 400 ppm, or up to 350 ppm, or up to 300 ppm, or up to 250 ppm, based on the weight of the liquid in the reaction medium of the primary oxidation zone. Manganese present in an amount ranging from 30 ppm to 400 ppm, or 70 ppm to 350 ppm, or 100 ppm to 350 ppm are especially desirable to promote high yield.

The weight ratio of cobalt atoms to manganese atoms in the reaction mixture can be from 1:1 to 400:1, or 10:1 to about 400:1. A catalyst system with improved Co:Mn ratio can lead to high yield of FDCA. To increase the yield of FDCA, when the oxidizable composition fed to the oxidation reactor comprises 5-HMF, then the cobalt to manganese weight ratio is at least 10:1, or at least 15:1, or at least 20:1, or at least 25:1, or at least 30:1, or at least 40:1 or at least 50:1, or at least 60:1, and in each case up to 400:1. However, in the case where the oxidizable composition comprises esters of 5-HMF, ethers of 5-HMF, or 5-alkyl furfurals, or mixtures of any of these compounds together or with 5-HMF, the cobalt to manganese weight ratio can be lowered while still obtaining high yield of FDCA, such as a weight ratio of Co:Mn of at least 1:1, or at least 2:1, or at least 5:1, or at least 9:1, or at least 10:1, or at least 15:1, or at least 20:1, or at least 25:1, or at least 30:1, or at least 40:1, or at least 50:1, or at least 60:1 and in each case up to 400:1.

The weight ratio of cobalt atoms to bromine atoms is desirably at least 0.7:1, or at least 0.8:1, or at least 0.9:1, or at least 1:1, or at least 1.05:1, or at least 1.2:1, or at least 1.5:1, or at least 1.8:1, or at least 2:1, or at least 2.2:1, or at least 2.4:1, or at least 2.6:1, or at least 2.8:1, and in each case up to 3.5, or up to 3.0, or up to 2.8.

The weight ratio of bromine atoms to manganese atoms is from about 2:1 to 500:1.

Desirably, the weight ratio of cobalt to manganese is from 10:1 to 400:1, and the weight ratio of cobalt to bromine atoms ranges from 0.7:1 to 3.5:1. Such a catalyst system with improved Co:Mn and Co:Br ratio can lead to high yield of FDCA (minimum of 90%), decrease in the formation of impurities (measured by b*) causing color in the downstream polymerization process while keeping the amount of CO and $CO_2$ (carbon burn) in the off-gas at a minimum.

Desirably, the amount of bromine present is at least 1000 ppm and up to 3500 ppm, and the weight ratio of bromine to manganese is from 2:1 to 500:1. This combination has the advantage of high yield and low carbon burn.

Desirably, the amount of bromine present is at least 1000 ppm and up to 3000 ppm, and the amount of cobalt present is at least 1000 ppm and up to 3000 ppm, and the weight ratio of cobalt to manganese is from 10:1 to 100:1. This combination has the advantage of high yield and low carbon burn.

Suitable solvents include aliphatic solvents. In an embodiment of the invention, the solvents are aliphatic carboxylic acids which include, but are not limited to, $C_2$ to $C_6$ monocarboxylic acids, e.g., acetic acid, propionic acid, n-butyric acid, isobutyric acid, n-valeric acid, trimethylacetic acid, caprioic acid, and mixtures thereof.

The most common solvent used for the oxidation is an aqueous acetic acid solution, typically having a concentration of 80 to 99 wt. %. In especially preferred embodiments, the solvent comprises a mixture of water and acetic acid which has a water content of 0% to about 15% by weight. Additionally, a portion of the solvent feed to the primary oxidation reactor may be obtained from a recycle stream obtained by displacing about 80 to 90% of the mother liquor taken from the crude reaction mixture stream discharged from the primary oxidation reactor with fresh, wet acetic acid containing about 0 to 15% water.

The oxidizing gas stream comprises oxygen. Examples include, but are not limited to, air and purified oxygen. The amount of oxygen in the primary oxidation zone ranges from about 5 mole % to 45 mole %, 5 mole % to 60 mole %, or 5 mole % to 80 mole %.

The temperature of the reaction mixture in the primary oxidation zone can vary from about 100° C. to about 220° C. The temperature of the reaction mixture in the primary oxidation zone is at least 100° C., or at least 105° C., or at least 110° C., or at least 115° C., or at least 120° C., or at least 125° C., or at least 130° C., or at least 135° C., or at least 140° C., or at least 145° C., or at least 150° C., or at least 155° C., or at least 160° C., and can be as high as 220° C., or up to 210° C., or up to 200° C., or up to 195° C., or up to 190° C., or up to 180° C., or up to 175° C., or up to 170° C., or up to 165° C., or up to 160° C., or up to 155° C., or up to 150° C., or up to 145° C., or up to 140° C., or up to 135° C., or up to 130° C. In other embodiments, the temperate ranges from 105° C. to 180° C., or from 105° C. to 175° C., or from 105° C. to 160° C., or from 105° C. to 165° C., or from 105° C. to 160° C., or from 105° C. to 155° C., or from 105° C. to 150° C., or from 110° C. to 180° C., or from 110° C. to 175° C., or from 110° C. to 170° C., or from 110° C. to 165° C., or from 110° C. to 160° C., or from 110° C. to 155° C., or from 110° C. to 150° C., or from 110° C. to 145° C., or from 115° C. to 180° C., or from 115° C. to 175° C., or from 115° C. to 170° C., or from 115° C. to 167° C., or from 115° C. to 160° C., or from 115° C. to 155° C., or from 110° C. to 150° C., or from 115° C. to 145° C., or from 120° C. to 180° C., or from 120° C. to 175° C., or from 120° C. to 170° C., or from 120° C. to 165° C., or from 120° C. to 160° C., or from 120° C. to 155° C., or from 120° C. to 150° C., or from 120° C. to 145° C., or from 125° C. to 180° C., or from 125° C. to 175° C., or from 125° C. to 170° C., or from 125° C. to 165° C., or from 125° C. to 160° C., or from 125° C. to 155° C., or from 125° C. to 150° C., or from 125° C. to 145° C., or from 130° C. to 180° C., or from 130° C. to 175° C., or from 130° C. to 170° C., or from 130° C. to 165° C., or from 130° C. to 160° C., or from 130° C. to 155° C., or from 130° C. to 150° C., or from 130° C. to 145° C., or from 135° C. to 180° C., or from 135° C. to 175° C., or from 135° C. to 170° C., or from 135° C. to 170° C., or from 135° C. to 165° C., or from 135° C. to 160° C., or from 135° C. to 155° C., or from 135° C. to 150° C., or from 135° C. to 145° C., or from 140° C. to 180° C., or from 140° C. to 175° C., or from 140° C. to 170° C., or from 140° C. to 170° C., or from 140° C. to 165° C., or from 140° C. to 160° C., or from 140° C. to 155° C., or from 140° C. to 150° C., or from 140° C. to 145° C., or from 145° C. to 180° C., or from 145° C. to 175° C., or from 145° C. to 170° C., or from 145° C. to 170° C., or from 145° C. to 165° C., or from 145° C. to 160° C., or from 145° C. to 155° C., or from 145° C. to 150° C., or from 150° C. to 180° C., or from 150° C. to 175° C., or from 150° C. to 170° C., or from 150° C. to 165° C., or from 150° C. to 160° C., or from 150° C. to 155° C., or from 155° C. to 180° C., or from 155° C. to 175° C., or from 155° C. to 170° C., or from 155° C. to 165° C., or from 155° C. to 160° C., or from 160° C. to 180° C., or from 160° C. to 175° C., or from 160° C. to 170° C., or from 160° C. to 165° C., or from 165° C. to 180° C., or from 165° C. to 175° C., or from 165° C. to 170° C., or from 165° C. to 180° C., or from 165° C. to 175° C., or from 165° C. to 170° C., or from 170° C. to 180° C., or from 170° C. to 175° C., or from 175° C. to 180° C.

To minimize carbon burn, it is desired that the temperature of the reaction mixture is not greater than 165° C., or not greater than 160° C. In the process of the invention, the contents of the oxidizer off gas comprise COx, wherein x is 1 or 2, and the amount of COx in the oxidizer off gas is less than 0.05 moles of COx per mole of the total oxidizable feed to the reaction medium, or no more than 4 moles of COx per mole of the total oxidizable feed to the reaction medium, or no more than 6 moles of COx per mole of the total oxidizable feed to the reaction medium. The carbon burn as determined by the COx generation rate can be calculated as follows: (moles of CO+moles of CO2)/moles of oxidizable feed. The low carbon burn generation rate in the process of the invention is achievable by the combination of low reaction temperature, and the molar weight ratios of the catalyst components as described above.

The oxidation reaction can be conducted under a pressure ranging from 40 to 300 psia. A bubble column is desirably operated under a pressure ranging from 40 psia to 150 psia. In a stirred tank vessel, the pressure is desirably set to 100 psia to 300 psia.

Oxidizer off gas stream 120 containing COx (CO and $CO_2$), water, nitrogen, and vaporized solvent, is routed to the oxidizer off gas treatment zone 800 to generate an inert gas stream 810, liquid stream 820 comprising water, and a recovered oxidation solvent stream 830 comprising condensed solvent. In one embodiment, oxidizer off gas stream 120 can be fed to directly, or indirectly after separating condensables such as solvent from non-condensables such as COx and nitrogen in a separation column (e.g. distillation column with 10-200 trays), to an energy recovery device such as a turbo-expander to drive an electric generator. Alternatively or in addition, the oxidizer off gas stream can be fed to a steam generator before or after the separation column to generate steam, and if desired, may then be fed to a turbo-expander and pre-heated prior to entry in the expander if necessary to ensure that the off gas does not condense in the turbo-expander.

In another embodiment, at least a portion of the oxidation solvent stream 830 recovered from the oxidizer off-gas stream is routed to a filter and then to a wash solvent stream 320 to become a portion of the wash solvent stream 320 for the purpose of washing the solids present in the solid-liquid separation zone. In another embodiment, the inert gas stream 810 can be vented to the atmosphere. In yet another embodiment, at least a portion of the inert gas stream 810 can be used as an inert gas in the process for inerting vessels and or used for convey gas for solids in the process.

The oxidation can be conducted in a continuous stirred tank reactor or in a bubble column reactor.

The FDCA formed by the oxidation reaction desirably precipitates out of the reaction mixture. The reaction mixture comprises the oxidizable composition, solvent, and catalyst if a homogeneous catalyst is used, otherwise it comprises the oxidizable composition and solvent.

The product of the oxidation reaction is a crude dicarboxylic acid stream 110 comprising FDCA as a solid, FDCA dissolved in the solvent, solvent, and by-products and intermediate products, and homogeneous catalyst system if used. Examples of by-products include levulinic acid, succinic acid, and acetoxy acetic acid. Examples of intermediate products include 5-formyl furan-2-carboxylic acid (FFCA) and 2,5-diformylfuran.

The percent solids in the crude dicarboxylic acid stream ranges is at least 10 wt %, or at least 15 wt. %, or at least 20 wt. %, or at least 25 wt. %, or at least 28 wt. %, or at least 30 wt. %, or at least 32 wt. %, or at least 35 wt. %, or at least 37 wt. %, or at least 40 wt. %. While there is no upper limit, as a practice the amount will not exceed 60 wt. %, or no greater than 55 wt. %, or no greater than 50 wt. %, or no greater than 45 wt. %, or not greater than 43 wt. %, or not greater than 40 wt %, or not greater than 39 wt. %.

The stated amount of each of the following intermediates, product, and impurities are based on the weight of the solids in the crude carboxylic acid composition produced in the primary oxidation reactor in the oxidation zone 100.

The amount of the intermediate FFCA present in the crude dicarboxylic acid stream is not particularly limited. Desirably, the amount is less than 4 wt. %, or less than 3.5 wt. %, or less than 3.0 wt. %, or less than 2.5 wt. %, or up to 2.0 wt. %, or up to 1.5 wt. %, or up to 1.0 wt. %, or up to 0.8 wt. %.

Impurities, if present in the crude dicarboxylic acid composition, include such compounds as 2,5-diformylfuran, levulinic acid, succinic acid, and acetoxy acetic acid. These compounds can be present, if at all, in an amount of 0 wt % to about 0.2 wt % 2,5diformylfuran, levulinic acid in an amount ranging from 0 wt % to 0.5 wt %, succinic acid in an amount ranging from 0 wt % to 0.5 wt % and acetoxy acetic acid in an amount ranging from 0 wt % to 0.5 wt %, and a cumulative amount of these impurities in an amount ranging from 0 wt. % to 1 wt. %, or from 0.01 wt % to 0.8 wt. %, or from 0.05 wt % to 0.6 wt. %.

In another embodiment of the invention the carboxylic acid composition 110 comprises FDCA, FFCA and 5-(ethoxycarbonyl)furan-2-carboxylic acid ("EFCA"). The EFCA in the carboxylic acid composition 110 can be present in an amount of at least 0.05 wt %, or at least 0.1 wt %, or at least 0.5 wt % and in each case up to about 4 wt %, or up to about 3.5 wt %, or up to 3 wt. %, or up to 2.5 wt %, or up to 2 wt. %.

The yield of FDCA, on a solids basis and measured after the drying zone step, is at least 60%, or at least 65%, or at least 70%, or at least 72%, or at least 74%, or at least 76%, or at least 78%, or at least 80%, or at least 81%, or at least 82%, or at least 83%, or at least 84%, or at least 85%, or at least 86%, or at least 87%, or at least 88%, or at least 89%, or at least 90%, or at least 91%, or at least 92%, or at least 94%, or at least 95%, and up to 99%, or up to 98%, or up to 97%, or up to 96%, or up to 95%, or up to 94%, or up to 93%, or up to 92%, or up to 91%, or up to 90%, or up to 89%. For example, the yield can range from 70% up to 99%, or 74% up to 98%, or 78% up to 98%, or 80% up to 98%, or 84% up to 98%, or 86% up to 98%, or 88% up to 98%, or 90% up to 98%, or 91% up to 98%, or 92% up to 98%, or 94% up to 98%, or 95% up to 99%.

Yield is defined as mass of FDCA obtained divided by the theoretical amount of FDCA that should be produced based on the amount of raw material use. For example, if one mole or 126.11 grams of 5-HMF are oxidized, it would theoretically generate one mole or 156.01 grams of FDCA. If for example, the actual amount of FDCA formed is only 150 grams, the yield for this reaction is calculated to be =(150/156.01) times 100, which equals a yield of 96%. The same calculation applies for oxidation reaction conducted using 5-HMF derivatives or mixed feeds.

The product purity of FDCA particles in a wet cake, or the purity of FDCA dried solid particles, obtainable is at least 90 wt % FDCA, or at least 92 wt % FDCA, or at least 94 wt % FDCA, or at least 96 wt % FDCA, or at least 98 wt % FDCA, based on the weight of the solids.

The maximum b* of the dried solids, or wet cake, is not particularly limited. However, a b* of not more than 20, or no more than 19, or no more than 18, or no more than 17, or no more than 16, or no more than 15, or no more than 10, or no more than 8, or no more than 6, or no more than 5, or no more than 4, or no more than 3, is desirable without having to subject the crude carboxylic acid composition to hydrogenation. However, if lowered b* is important for a particular application, the crude carboxylic acid composition can be subjected to hydrogenation.

The b* is one of the three-color attributes measured on a spectroscopic reflectance-based instrument. The color can be measured by any device known in the art. A Hunter Ultrascan XE instrument is typically the measuring device. Positive readings signify the degree of yellow (or absorbance of blue), while negative readings signify the degree of blue (or absorbance of yellow).

In the next step, which is an optional step, the crude dicarboxylic acid stream 110 can fed to a cooling zone 200 to generate a cooled crude dicarboxylic acid slurry stream 210 and a 1st solvent vapor stream 220 comprising solvent vapor. The cooling of crude carboxylic slurry stream 110 can be accomplished by any means known in the art. Typically, the cooling zone 200 is a flash tank. All or a portion of the crude dicarboxylic acid stream 110 can be fed to the cooling zone.

All or a portion of the crude dicarboxylic acid stream 110 can be fed to solid-liquid separation zone 300 without first being fed to a cooling zone 200. Thus, none or only a portion can be cooled in cooling zone 200. The temperature of stream 210 exiting the cooling zone can range from 35° C. to 160° C., 55° C. to 120° C., and preferably from 75° C. to 95° C.

The crude dicarboxylic acid stream 110, or 210 if routed through a cooling zone, is fed to a solid-liquid separation zone 300 to generate a crude carboxylic acid wet cake stream 310 comprising FDCA. The functions of isolating, washing and dewatering the crude carboxylic acid stream may be accomplished in a single solid-liquid separation device or multiple solid-liquid separation devices. The solid-liquid separation zone 300 comprises at least one solid-liquid separation device capable of separating solids and liquids, washing solids with a wash solvent stream 320, and reducing the % moisture in the washed solids to less than 30 weight %. Desirably, the solid-liquid separation device is capable of reducing the % moisture down to less than 20 weight %, or less than 15 weight %, and preferably 10 weight % or less. Equipment suitable for the solid liquid separation zone can typically be comprised of, but not limited to, the following types of devices: centrifuges of all types including but not limited to decanter and disc stack centrifuges, solid bowl centrifuges, cyclone, rotary drum filter, belt filter, pressure leaf filter, candle filter, and the like. The preferred solid liquid separation device for the solid liquid separation zone is a continuous pressure drum filter, or more specifically a continuous rotary pressure drum filter. The solid-liquid separator may be operated in continuous or batch mode, although it will be appreciated that for commercial processes, the continuous mode is preferred.

The temperature of crude carboxylic acid slurry stream, if cooled as stream 210, fed to the solid-liquid separation zone 300 can range from 35° C. to 160° C., 55° C. to 120° C., and is preferably from 75° C. to 95° C. The wash stream 320 comprises a liquid suitable for displacing and washing mother liquor from the solids. For example, the wash solvent comprises acetic acid, or acetic acid and water, an alcohol, or water, in each case up to an amount of 100%. The temperature of the wash solvent can range from 20° C. to 180° C., or 40° C. and 150° C., or 50° C. to 130° C. The amount of wash solvent used is defined as the wash ratio and equals the mass of wash divided by the mass of solids on a batch or continuous basis. The wash ratio can range from about 0.3 to about 5, about 0.4 to about 4, and preferably from about 0.5 to 3.

After solids are washed in the solid liquid separation zone 300, they are dewatered. Dewatering can take place in the solid liquid separation zone or it can be a separate device from the solid-liquid separation device. Dewatering involves reducing the mass of moisture present with the solids to less than 30% by weight, less than 25% by weight, less than 20% by weight, and most preferably less than 15% by weight so as to generate a crude carboxylic acid wet cake stream 310 comprising FDCA. Dewatering can be accomplished in a filter by passing a gas stream through the solids to displace free liquid after the solids have been washed with a wash solvent. Alternatively, dewatering can be achieved by centrifugal forces in a perforated bowl or solid bowl centrifuge.

One or more washes may be implemented in solid-liquid separation zone 300. One or more of the washes, preferably at least the final wash, in solid-liquid separation zone 300 comprises a hydroxyl functional compound as defined further below, such as an alcohol (e.g. methanol). By this method, a wet cake stream 310 is produced comprising the hydroxyl functional compound such as methanol in liquid form. The amount of the hydroxyl functional compound in liquid form in the wet cake can be at least 50 wt %, or at least 75 weight %, or at least 85% weight %, or at least 95 weight % hydroxyl functional compound such as methanol based on the weight of the liquids in the wet cake stream. The advantage of adopting this technique of washing with a hydroxyl functional compound is that a portion or all of the wet cake can be fed to the esterification zone 500 without undergoing, or by-pass, a step of feeding the wet cake to a vessel for drying the wet cake in a drying zone 400 after the solid-liquid separation zone.

In one embodiment, 100% of wet cake stream 310 is fed to esterification reaction zone 500 without undergoing or subjecting the wet cake to a vessel for drying the wet cake from the solid liquid separation zone 300.

Stream 330 generated in solid-liquid separation zone 300 is a liquid mother liquor stream comprising oxidation solvent, catalyst, and impurities. If desired, a portion of mother liquor stream 330 can be fed to a purge zone 900 and a portion can be fed back to the primary oxidation zone 100, wherein a portion is at least 5 weight % based on the weight of the liquid. Wash liquor stream 340 is also generated in the solid-liquid separation zone 300 and comprises a portion of the mother liquor present in stream 210 and wash solvent wherein the weight ratio of mother liquor mass to wash solvent mass in the wash liquor stream is less than 3 and preferably less than 2. From 5% to 95%, from 30% to 90%, and most preferably from 40 to 80% of mother liquor present in the crude carboxylic acid stream fed to the solid-liquid separation zone 200 is isolated in solid-liquid separation zone 300 to generate mother liquor stream 330 resulting in dissolved matter comprising impurities present in the displaced mother liquor not going forward in the process. The mother liquor stream 330 contains dissolved impurities removed from the crude dicarboxylic acid.

Sufficient wash solvent is fed to the solid liquid separation zone 300 that becomes mixed with solids present resulting in a low impurity slurry stream 310 being pumpable with weight % solids ranging from 1% to 50%, 10% to 40%, and preferably the weight % solids in stream 310 will range from 25% to 38%.

In one embodiment, from 5% to 100% by weight of the displaced mother liquor stream 330 is routed to a purge zone 900 wherein a portion of the impurities present in stream 330 are isolated and exit the process as purge stream 920, wherein a portion is 5% by weight or greater. Recovered solvent stream 910 comprises solvent and catalyst isolated from stream 330 and is recycled to the process. The recovered solvent stream 910 can be recycled to the primary oxidation zone 100 and contains greater than 30% of the catalyst that entered the purge zone 900 in stream 330. The stream 910 recycled to the primary oxidation zone 100 may contain greater than 50 weight %, or greater than 70 weight %, or greater than 90 weight % of the catalyst that enters the purge zone 900 in stream 330 on a continuous or batch basis.

Optionally, a portion up to 100% of the crude carboxylic acid composition may be routed directly to a secondary oxidation zone (not shown) before being subjected to a solid liquid separation zone 300.

Generally, oxidation in a secondary oxidation zone is at a higher temperature than the oxidation in the primary oxidation zone 100 to enhance the impurity removal. In one embodiment, the secondary oxidation zone is operated at about 30° C., 20° C., and preferably 10° C. higher temperature than the oxidation temperature in the primary oxidation zone 100 to enhance the impurity removal. The secondary oxidation zone can be heated directly with solvent vapor, or steam via stream or indirectly by any means known in the art.

Additional purification of the crude carboxylic acid stream can be accomplished in the secondary oxidation zone by a mechanism involving recrystallization or crystal growth and oxidation of impurities and intermediates including FFCA. One of the functions of the secondary oxidation zone is to convert FFCA to FDCA. FFCA is considered monofunctional relative to a polyester condensation reaction because it contains only one carboxylic acid. FFCA is present in the crude carboxylic acid composition stream. FFCA is generated in the primary oxidation zone 100 because the reaction of 5-HMF to FFCA can be about eight times faster than the reaction of FFCA to the desired di-functional product FDCA. Additional air or molecular oxygen may be fed to the secondary oxidation zone in an amount necessary to oxidize a substantial portion of the partially oxidized products such as FFCA to the corresponding carboxylic acid FDCA. Generally, at least 70% by weight, or at least 80 wt %, or at least 90 wt % of the FFCA present in the crude carboxylic acid composition exiting the primary oxidation zone can be converted to FDCA in the secondary oxidation zone. Significant concentrations of monofunctional molecules like FFCA in the dried, purified FDCA product are particularly detrimental to polymerization processes as they may act as chain terminators during the polyester condensation reaction.

If a secondary oxidation zone is employed, the secondary oxidation slurry can be crystallized to form a crystallized slurry stream. Vapor from the crystallization zone can be condensed in at least one condenser and returned to the crystallization zone or recycled, or it can be withdrawn or sent to an energy recovery device. The crystallizer off-gas can be removed and routed to a recovery system where the solvent is removed, and crystallizer off gas containing VOC's may be treated, for example, by incineration in a catalytic oxidation unit. The crystallizer can be operated by cooling the secondary oxidation slurry to a temperature between about 40° C. to about 175° C. to form a crystallized slurry stream.

The crystallized slurry stream can then be subjected to a cooling zone 200 if desired and the process continued as described above.

Instead of using a wet cake, one may produce a dried solid. The wet cake produced in the solid liquid separation zone 300 can be dried in a drying zone 400 to generate a dry purified carboxylic acid solid 410 and a vapor stream 420. The vapor stream 420 typically comprises the wash solvent vapor used in the solid liquid separation zone, and may additionally contain the solvent used in the primary oxidation zone. The drying zone 400 comprises at least one dryer and can be accomplished by any means known in the art that is capable of evaporating at least 10% of the volatiles remaining in the purified wet cake stream to produce the dried, purified carboxylic acid solids. For example, indirect contact dryers include, but are not limited to, a rotary steam tube dryer, a Single Shaft Porcupine dryer, and a Bepex Solidaire dryer. Direct contact dryers include, but are not limited to, a fluid bed dryer and drying in a convey line.

The dried, purified carboxylic acid solids comprising purified FDCA can be a carboxylic acid composition with less than 8% moisture, preferably less than 5% moisture, and more preferably less than 1% moisture, and even more preferably less than 0.5%, and yet more preferably less than 0.1%.

A vacuum system can be utilized to draw vapor stream 420 from the drying zone 400. If a vacuum system is used in this fashion, the pressure at the dryer outlet can range from about 760 mmHg to about 400 mmHg, from about 760 mmHg to about 600 mmHg, from about 760 mmHg to about 700 mmHg, from about 760 mmHg to about 720 mmHg, and from about 760 mmHg to about 740 mmHg wherein pressure is measured in mmHg above absolute vacuum.

The dried, purified carboxylic acid solids, or the solids in the wet cake, desirably have a b* less than about 9.0, or less than about 6.0, or less than about 5.0, or less than about 4.0. or less than about 3.

It should be appreciated that the process zones previously described can be utilized in any other logical order to produce the dried, purified carboxylic acid. It should also be appreciated that when the process zones are reordered that the process conditions may change. It is also understood that all percent values are weight percents.

One function of drying zone 400 is to remove by evaporation oxidation solvent comprising a mono-carboxylic acid with 2 to 6 carbons that can be present in the crude carboxylic acid wet cake stream 310. The % moisture in crude carboxylic acid wet cake stream 310 typically ranges from 4.0% by weight to 30% by weight depending on the operation conditions of the solid-liquid separation zone 300. If for example, the liquid portion of stream 310 is about 90% acetic acid, the amount of acetic acid present in stream 310 can range from about 3.6 weight % to 27 weight %. It is desirable to remove acetic acid prior to esterification zone 500 because acetic acid will react with the alcohol present in the zone 500 to create unwanted by products. For example, if methanol is fed to esterification zone 500 for the purpose of reacting with FDCA, it will also react with acetic acid present to form methyl acetate and therefore consume methanol and generate an unwanted by-product. It is desirable to minimize the acetic acid content of the crude carboxylic acid stream comprising FDCA that is fed to esterification zone 500 to less than 3.6 weight %, preferably less than 1 weight %, and more preferably less than 0.5 weight %, and most preferably less than 0.1 weight %. One method for achieving this is to dry a crude carboxylic acid wet cake stream 310 comprising acetic acid prior to routing the crude carboxylic to esterification zone 500. Another method for minimizing the oxidation solvent comprising mono-carboxylic acid with carbons ranging from 2 to 5 in the crude carboxylic acid stream 410 routed to esterification zone 500 to an acceptable level without utilizing a dryer zone 400 is to conduct non-monocarboxylic acid wash or washes in solid-liquid separation zone 300 to wash the oxidation solvent from the solids with a wash comprising any wash solvent compatible with the esterification zone 500 chemistry to generate a crude carboxylic acid wet cake stream 310 suitable for routing directly to esterification zone 500 without being dried in drying zone 400. Acceptable wash solvents comprise solvents that do not make undesirable by products in esterification zone 500. For example, water is an acceptable wash solvent to displace acetic acid from solids in solid-liquid separation zone 300. Another acceptable wash solvent is an alcohol that will be used as a reactant in the esterification zone 500. There can be multiple and separate washes in the solid liquid separation zone 300. A wash feed can comprise water up to 100 weight %. A wash feed can comprise an alcohol up to 100 weight %. A wash feed can comprise methanol up to 100%. A wash feed can comprise the same alcohol utilized in the esterification zone 500 for reaction with FDCA to form the di-ester product. In one embodiment, a wet cake dewatering step can be used after the wet cake is formed in the solid liquid separation zone 300 and before any non-acetic acid wash is employed. This dewatering step will minimize the liquid content of the wet cake prior to washing with a non-acetic acid wash solvent such as water and or methanol as described above, thus minimizing the cost to separate any mixtures of acetic acid and non-acetic acid wash solvents that are generated in solid-liquid separation zone 300.

The solid dicarboxylic acid composition 410, which can be either dried carboxylic acid solids or wet cake, comprising FDCA, and the alcohol composition stream 520 are fed to the esterification reaction zone 500. The solid dicarboxylic acid composition 410 can be shipped via truck, ship, or rail as solids. However, an advantage of the invention is that the process for the oxidation of the oxidizable material containing the furan group can be integrated with the process for the manufacture of the crude diester composition.

An integrated process includes co-locating the two manufacturing facilities, one for oxidation and the other for esterification, within 10 miles, or within 5 miles, or within 2 miles, or within 1 mile, or within ½ mile of each other. An integrated process also includes having the two manufacturing facilities in solid or fluid communication with each other. If a solid dicarboxylic acid composition is produced, the solids can be conveyed by any suitable means, such as air or belt, to the esterification facility. If a wet cake dicarboxylic acid composition is produced, the wet cake can be moved by belt or pumped as a liquid slurry to the facility for esterification.

What we claim is:

1. A vapor stream discharged from a rectification zone of a dialkyl furan-2,5-dicarboxylate (DAFD) manufacturing process, said vapor stream comprising:
   a. at least 2 wt. % alcohol;
   b. at least 1 wt. % DAFD;
   c. at least 0.5 wt. % water; and
   d. from zero up to 3 wt. % 5-(alkoxycarbonyl)furan-2-carboxylic acid (ACFC),
   wherein said vapor stream has an ACFC:DAFD molar ratio not greater than 0.5:1.

2. The vapor stream of claim 1, further comprising at least 0.5 wt. % alkyl furan-2-carboxylate (AFC).

3. The vapor stream of claim 1, further comprising at least 0.01 wt. % alkyl 5-formylfuran-2-carboxylate (AFFC).

4. The vapor stream of claim 1, wherein said alcohol is present in said vapor stream in an amount from at least 5 wt. % up to 50 wt. %, wherein said DAFD is present in said vapor stream in an amount from at 2 wt. % least up to 50 wt. %, wherein said water is present in said vapor stream in an amount from at least 2 wt. % up to 15 wt. %, wherein said ACFC is present in said vapor stream in an amount from zero up to 2 wt. %, wherein said vapor stream has an ACFC:DAFD molar ratio not greater than 0.05:1.

5. The vapor stream of claim 4, further comprising from at least 1 wt. % up to 6 wt. % AFC and further comprising from at least 0.1 wt. % up to 3 wt. % AFFC.

6. The vapor stream of claim 1, wherein said vapor stream has an ACFC:DAFD molar ratio not greater than 0.01:1.

7. The vapor stream of claim 1, wherein said vapor stream has an ACFC:DAFD molar ratio not greater than 0.005:1.

8. The vapor stream of claim 1, wherein said vapor stream has an ACFC:DAFD molar ratio not greater than 0.001:1.

9. The vapor stream of claim 1, wherein said alcohol is present in said vapor stream in an amount from at least 15 wt. % up to 30 wt. %.

10. The vapor stream of claim 1, wherein said DAFD is present in said vapor stream in an amount from at 3 wt. % least up to 40 wt. %.

11. The vapor stream of claim 1, wherein said water is present in said vapor stream in an amount from at least 5 wt. % up to 10 wt. %.

12. The vapor stream of claim 1, wherein said ACFC is present in said vapor stream in an amount from zero up to 100 ppm.

13. The vapor stream of claim 1, further comprising from at least 1 wt. % up to 5 wt. % AFC.

14. The vapor stream of claim 1, further comprising from at least 0.1 wt. % up to 2 wt. % AFFC.

15. The vapor stream of claim 1, wherein said alcohol is present in said vapor stream in an amount from at least 15 wt. % up to 30 wt. %, wherein said DAFD is present in said vapor stream in an amount from at 3 wt. % least up to 40 wt. %, wherein said water is present in said vapor stream in an amount from at least 5 wt. % up to 10 wt. %, wherein said ACFC is present in said vapor stream in an amount from zero up to 100 ppm.

16. The vapor stream of claim 15, wherein said vapor stream has an ACFC:DAFD molar ratio not greater than 0.01:1.

17. The vapor stream of claim 15, further comprising from at least 1 wt. % up to 5 wt. % AFC.

18. The vapor stream of claim 15, further comprising from at least 0.1 wt. % up to 2 wt. % AFFC.

19. The vapor stream of claim 15, further comprising from at least 1 wt. % up to 5 wt. % AFC and further comprising from at least 0.1 wt. % up to 2 wt. % AFFC.

20. The vapor stream of claim 19, wherein said vapor stream has an ACFC:DAFD molar ratio not greater than 0.01:1.

* * * * *